(12) United States Patent
Matsumoto et al.

(10) Patent No.: US 11,980,391 B2
(45) Date of Patent: May 14, 2024

(54) PUNCTURE NEEDLE, ULTRASOUND DIAGNOSTIC APPARATUS, AND CONTROL METHOD OF ULTRASOUND DIAGNOSTIC APPARATUS

(71) Applicant: FUJIFILM Corporation, Tokyo (JP)

(72) Inventors: Tsuyoshi Matsumoto, Kanagawa (JP); Tomoki Inoue, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 243 days.

(21) Appl. No.: 17/358,865

(22) Filed: Jun. 25, 2021

(65) Prior Publication Data
US 2021/0322054 A1 Oct. 21, 2021

Related U.S. Application Data

(63) Continuation of application No. PCT/JP2019/035305, filed on Sep. 9, 2019.

(30) Foreign Application Priority Data

Jan. 17, 2019 (JP) .................. 2019-005987

(51) Int. Cl.
*A61B 17/34* (2006.01)
*A61B 8/00* (2006.01)
*A61B 34/20* (2016.01)

(52) U.S. Cl.
CPC .......... *A61B 17/3403* (2013.01); *A61B 8/463* (2013.01); *A61B 34/20* (2016.02);
(Continued)

(58) Field of Classification Search
CPC ................ A61B 10/02; A61B 17/3403; A61B 2017/3413; A61B 2034/2063;
(Continued)

(56) References Cited

U.S. PATENT DOCUMENTS 4,582,061 A 4/1986 Fry
2006/0247530 A1 11/2006 Hardin et al.
(Continued)

FOREIGN PATENT DOCUMENTS

CN 104939865 A 9/2015
CN 107224317 A 10/2017
(Continued)

OTHER PUBLICATIONS

International Search Report issued in PCT/JP2019/035305; dated Nov. 26, 2019.
(Continued)

*Primary Examiner* — Joseph M Santos Rodriguez
*Assistant Examiner* — Maria Christina Talty
(74) *Attorney, Agent, or Firm* — Studebaker & Brackett PC (57) ABSTRACT

A puncture needle includes a shaft part, a needle tip part disposed at a tip of the shaft part, and a plurality of processed parts that are arranged on an outer peripheral part of the shaft part along a length direction of the shaft part and form a geometric progression with a geometric ratio of 2 in which arrangement intervals gradually decrease toward the needle tip part, in which a distance between a reference point which is located on a needle tip part side from a first processed part closest to the needle tip part among the plurality of processed parts and is located at a predetermined distance from the needle tip part and the first processed part is equal to an arrangement interval between the first processed part and a second processed part which is second closest to the needle tip part.

11 Claims, 7 Drawing Sheets

(52) U.S. Cl.
CPC .............. *A61B 2017/3413* (2013.01); *A61B 2034/2063* (2016.02)

(58) Field of Classification Search
CPC ...... A61B 2034/2065; A61B 2090/378; A61B 34/20; A61B 8/0841; A61B 8/463; A61B 8/565; A61M 5/158
See application file for complete search history.

(56) References Cited

U.S. PATENT DOCUMENTS

| | | |
|---|---|---|
| 2008/0249416 A1 | 10/2008 | Sato |
| 2010/0168684 A1* | 7/2010 | Ryan ................ A61B 17/3403 604/272 |
| 2014/0265024 A1 | 9/2014 | Quearry |
| 2014/0336687 A1 | 11/2014 | Iwase et al. |
| 2015/0272700 A1 | 10/2015 | Masuda et al. |
| 2016/0367322 A1* | 12/2016 | Jain ........................ G01S 15/74 |
| 2017/0020562 A1* | 1/2017 | Erkamp ............ A61M 25/0108 |
| 2017/0112528 A1* | 4/2017 | Crisman ............ A61B 17/3423 |

FOREIGN PATENT DOCUMENTS

| | | |
|---|---|---|
| JP | 2008-253581 A | 10/2008 |
| JP | 2011-125632 A | 6/2011 |
| JP | 2013-027513 A | 2/2013 |
| JP | 2013-116288 A | 6/2013 |
| JP | 2016-516469 A | 6/2016 |
| WO | 2018/054969 A1 | 3/2018 |

OTHER PUBLICATIONS

International Preliminary Report On Patentability and Written Opinion issued in PCT/JP2019/035305; dated Jun. 16, 2021.
The extended European search report issued by the European Patent Office dated Feb. 22, 2022, which corresponds to European Patent Application No. 19910115.5-1126 and is related to U.S. Appl. No. 17/358,865.
An Office Action mailed by China National Intellectual Property Administration dated Sep. 27, 2023, which corresponds to Chinese Patent Application No. 2201980089336.0 and is related to U.S. Appl. No. 17/358,865; with English language translation.

* cited by examiner

PUNCTURE NEEDLE, ULTRASOUND DIAGNOSTIC APPARATUS, AND CONTROL METHOD OF ULTRASOUND DIAGNOSTIC APPARATUS

CROSS-REFERENCE TO RELATED APPLICATIONS

This application is a Continuation of PCT International Application No. PCT/JP2019/035305 filed on Sep. 9, 2019, which claims priority under 35 U.S.C. § 119(a) to Japanese Patent Application No. 2019-005987 filed on Jan. 17, 2019. Each of the above application(s) is hereby expressly incorporated by reference, in its entirety, into the present application.

BACKGROUND OF THE INVENTION

1. Field of the Invention

The present invention relates to a puncture needle, an ultrasound diagnostic apparatus that detects a puncture needle inserted into a subject, and a control method of the ultrasound diagnostic apparatus.

2. Description of the Related Art

There is a technique of inserting a so-called puncture needle into a subject in order to place a catheter in the subject. In recent years, a method of inserting a puncture needle into a subject while observing the puncture needle inserted into the subject using an ultrasound diagnostic apparatus is often used.

In general, the ultrasound diagnostic apparatus comprises an ultrasound probe provided with a transducer array in which a plurality of elements are arranged. In a state where the ultrasound probe is brought into contact with a body surface of the subject, an ultrasound beam is transmitted from the transducer array toward an inside of the subject, and an ultrasound echo from the subject is received by the transducer array to obtain element data. Further, the ultrasound diagnostic apparatus electrically processes the obtained element data to generate an ultrasound image for a relevant part of the subject.

Here, since the puncture needle is usually inserted in an inclined state with respect to the body surface of the subject, the ultrasound echo reflected from the puncture needle in the subject is difficult to propagate toward the ultrasound probe, and the puncture needle is sometimes not clearly depicted in the ultrasound image. Therefore, in order to clearly depict the puncture needle in the ultrasound image, for example, as disclosed in JP2011-125632A, a puncture needle which is processed to reflect an ultrasound beam from an ultrasound probe has been developed. A plurality of grooves for reflecting an ultrasound beam are formed on an outer peripheral part of the puncture needle of JP2011-125632A. In a case where the puncture needle of JP2011-125632A is inserted into a subject and the inserted puncture needle is irradiated with an ultrasound beam, the ultrasound beam applied to the puncture needle is reflected by the plurality of grooves formed in the puncture needle and propagates toward the ultrasound probe. Thus, the plurality of grooves formed in the puncture needle are depicted in the ultrasound image.

SUMMARY OF THE INVENTION

However, since a groove cannot be formed at a tip part of a sharply pointed puncture needle, a user such as a doctor cannot clearly grasp the tip part of the puncture needle even by observing an ultrasound image depicting a plurality of grooves of the puncture needle, and therefore, it is sometimes difficult to guide the tip part of the puncture needle to a desired place.

In addition, the groove of the puncture needle on the ultrasound image is sometimes concealed or disappears due to a high-intensity reflection signal, an acoustic shadow, or the like derived from a tissue in a subject. Thus, a position of the groove in the puncture needle is not specified, and it is sometimes difficult for the user to estimate a position of the tip part of the puncture needle.

The present invention has been made to solve such a conventional problem, and an object of the present invention is to provide a puncture needle, an ultrasound diagnostic apparatus, and a control method of the ultrasound diagnostic apparatus, with which a user can accurately grasp a tip part of the puncture needle.

In order to achieve the above object, a puncture needle according to a first aspect of the present invention comprises a shaft part, a needle tip part disposed at a tip of the shaft part, and a plurality of processed parts that are arranged on an outer peripheral part of the shaft part along a length direction of the shaft part and form a geometric progression with a geometric ratio of 2 in which arrangement intervals gradually decrease toward the needle tip part, in which a distance between a reference point, which is located on a needle tip part side from a first processed part closest to the needle tip part among the plurality of processed parts and is located at a predetermined distance from the needle tip part, and the first processed part is equal to an arrangement interval between the first processed part and a second processed part which is second closest to the needle tip part.

It is preferable that the predetermined distance is 0, and the reference point is the needle tip part.

In addition, it is preferable that the plurality of processed parts are grooves formed along an entire periphery of the shaft part.

An ultrasound diagnostic apparatus according to a second aspect of the present invention comprises a display unit that displays an ultrasound image in which the puncture needle is captured, an arrangement interval detection unit that recognizes the plurality of processed parts of the puncture needle and detects the arrangement intervals of the plurality of processed parts by image analysis of the ultrasound image, a geometric progression determination unit that determines whether or not the arrangement intervals of the plurality of processed parts detected by the arrangement interval detection unit form the geometric progression with a geometric ratio of 2, and a needle tip part position estimation unit that detects, as the reference point, a point extending from an arrangement position of an optional processed part among the plurality of processed parts to a tip side of the shaft part by an arrangement interval between the optional processed part and a processed part adjacent to a base end side of the shaft part with respect to the optional processed part and estimates a position of the needle tip part based on a position of the detected reference point, in a case where the geometric progression determination unit determines that the geometric progression is formed.

The display unit may display the ultrasound image in which the puncture needle having the reference point as the needle tip part is captured, and the needle tip part position estimation unit may estimate the position of the reference point as the position of the needle tip part.

Alternatively, the needle tip part position estimation unit may estimate a point extending from the position of the reference point to the tip side of the shaft part by the predetermined distance as the position of the needle tip part.

In addition, it is preferable that the needle tip part position estimation unit displays the estimated position of the needle tip part on the display unit.

The ultrasound diagnostic apparatus may further comprise an ultrasound probe and an image acquisition unit that acquires the ultrasound image by performing transmission and reception of an ultrasound beam between the ultrasound probe and a subject. The display unit may display the ultrasound image acquired by the image acquisition unit, and the arrangement interval detection unit may recognize the plurality of processed parts of the puncture needle and detect the arrangement intervals of the plurality of processed parts by image analysis of the ultrasound image acquired by the image acquisition unit.

A control method of an ultrasound diagnostic apparatus according to a third aspect of the present invention comprises displaying an ultrasound image in which the puncture needle is captured, recognizing the plurality of processed parts of the puncture needle and detecting the arrangement intervals of the plurality of processed parts by image analysis of the ultrasound image, determining whether or not the detected arrangement intervals of the plurality of processed parts form the geometric progression with a geometric ratio of 2, detecting, as the reference point, a point extending from an arrangement position of an optional processed part among the plurality of processed parts to a tip side of the shaft part by an arrangement interval between the optional processed part and a processed part adjacent to a base end side of the shaft part with respect to the optional processed part, in a case where determination is made that the geometric progression is formed, and estimating a position of the needle tip part based on a position of the detected reference point.

According to the present invention, a puncture needle comprises a shaft part, a needle tip part disposed at a tip of the shaft part, and a plurality of processed parts that are arranged on an outer peripheral part of the shaft part along a length direction of the shaft part and form a geometric progression with a geometric ratio of 2 in which arrangement intervals gradually decrease toward the needle tip part, in which a distance between a reference point, which is located on a needle tip part side from a first processed part closest to the needle tip part among the plurality of processed parts and is located at a predetermined distance from the needle tip part, and the first processed part is equal to an arrangement interval between the first processed part and a second processed part which is second closest to the needle tip part. Therefore, a user can accurately grasp the tip part of the puncture needle.

DESCRIPTION OF THE PREFERRED EMBODIMENTS

Hereinafter, embodiments of the present invention will be described with reference to the accompanying drawings.

Description of constituents described below may be made based on a typical embodiment of the present invention, but the present invention is not limited to such an embodiment.

Embodiment 1

Figure 1:
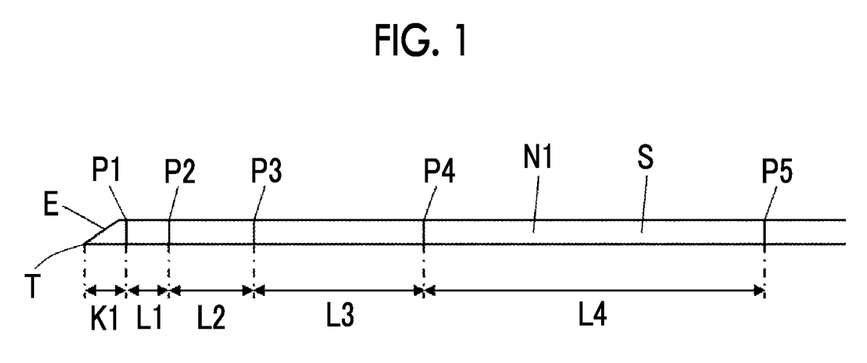
FIG. 1 is a diagram showing a puncture needle according to Embodiment 1 of the present invention.

FIG. 1 shows a puncture needle N1 according to Embodiment 1 of the present invention. The puncture needle N1 is inserted into a subject in order to place a catheter, a drug, or the like in the subject, and comprises a shaft part S and a sharp needle tip part T formed by obliquely cutting out a tip part of the shaft part S and disposed at a tip of the shaft part S. In the shaft part S, a plurality of processed parts P1 to P5 formed of grooves formed to surround a periphery of the shaft part S are arranged and formed along a length direction of the shaft part S. In addition, an arrangement interval L1 between the first processed part P1 and the second processed part P2, an arrangement interval L2 between the second processed part P2 and the third processed part P3, an arrangement interval L3 between the third processed part P3 and the fourth processed part P4, and an arrangement interval L4 between the fourth processed part P4 and the fifth processed part P5 form a geometric progression with a geometric ratio of 2 in which values gradually decrease toward the needle tip part T. Therefore, a ratio of the arrangement interval L2 to the arrangement interval L1, a ratio of the arrangement interval L3 to the arrangement interval L2, and a ratio of the arrangement interval L4 to the arrangement interval L3 are 2, respectively. Here, the term "the arrangement intervals form the geometric progression" means that values of the arrangement intervals form the geometric progression, and that in a case where values of the arrangement intervals L1 to L6 are integers and are aligned to a specific unit such as mm, the values form the geometric progression.

The first processed part P1 closest to the needle tip part T is formed at a position separated by a distance K1 from the needle tip part T, and the distance K1 between the needle tip part T and the first processed part P1 is designed to be equal to the arrangement interval L1 between the first processed part P1 and the second processed part P2 which is second closest to the needle tip part T.

For example, specifically, assuming that the distance k1 from the needle tip part T to the first processed part P1 is 5 mm, the arrangement interval L1 between the first processed part P1 and the second processed part P2 is 5 mm, the arrangement interval L2 between the second processed part P2 and the third processed part P3 is 10 mm, the arrangement interval L3 between the third processed part P3 and the fourth processed part P4 is 20 mm, and the arrangement interval L4 between the fourth processed part P4 and the fifth processed part P5 is 40 mm, the first processed part P1 to the fifth processed part P5 can be formed such that the distance K1 from the needle tip part T to the first processed part P1 is equal to the arrangement interval L1 between the first processed part P1 and the second processed part P2 and the arrangement intervals L1 to L4 form a geometric progression with a geometric ratio of 2.

In addition, as shown in FIG. 1, since the needle tip part T is formed by obliquely cutting out the tip part of the shaft part S, an inclined surface E inclined by a predetermined inclination angle with respect to an extending direction of the shaft part S is formed at a tip part of the shaft part S, and the first processed part P1 is formed on a base end side of the shaft part S from the inclined surface E. Therefore, a formation position of the first processed part P1 can be appropriately set according to the specifications of the puncture needle N1, such as an outer diameter of the shaft part S and the inclination angle of the inclined surface E with respect to the extending direction of the shaft part S.

Figure 2:
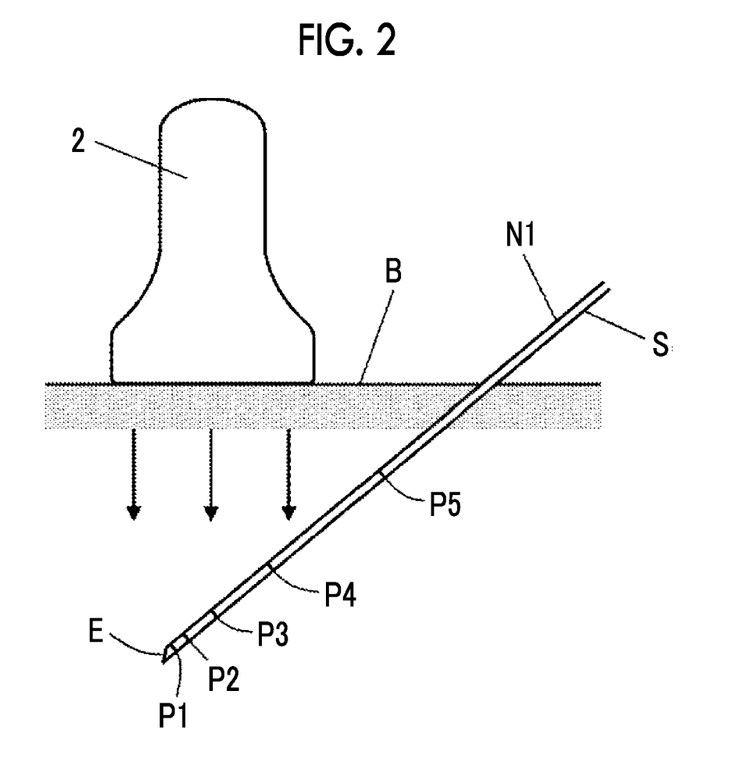
FIG. 2 is a diagram schematically showing a state where the puncture needle according to Embodiment 1 of the present invention is inserted into a subject and the puncture needle is irradiated with an ultrasound beam.

As shown in FIG. 2, the puncture needle N1 according to Embodiment 1 of the present invention as described above is irradiated with an ultrasound beam from an ultrasound probe 2 in contact with a body surface B of the subject while being inserted into the subject. The ultrasound beam applied to the puncture needle is reflected by the plurality of processed parts P1 to P5, and the reflected ultrasound beam propagates toward the ultrasound probe 2. Thus, in a case where the puncture needle N1 is imaged by the ultrasound probe 2, a plurality of processed parts P1 to P5 of the puncture needle N1 are depicted in an ultrasound image.

Here, in the puncture needle N1 according to Embodiment 1 of the present invention, since the first processed part P1 is formed on the base end side of the shaft part S from the inclined surface E, the first processed part P1 can be depicted in the ultrasound image regardless of a rotation angle around a central axis of the puncture needle N1.

Figure 3:
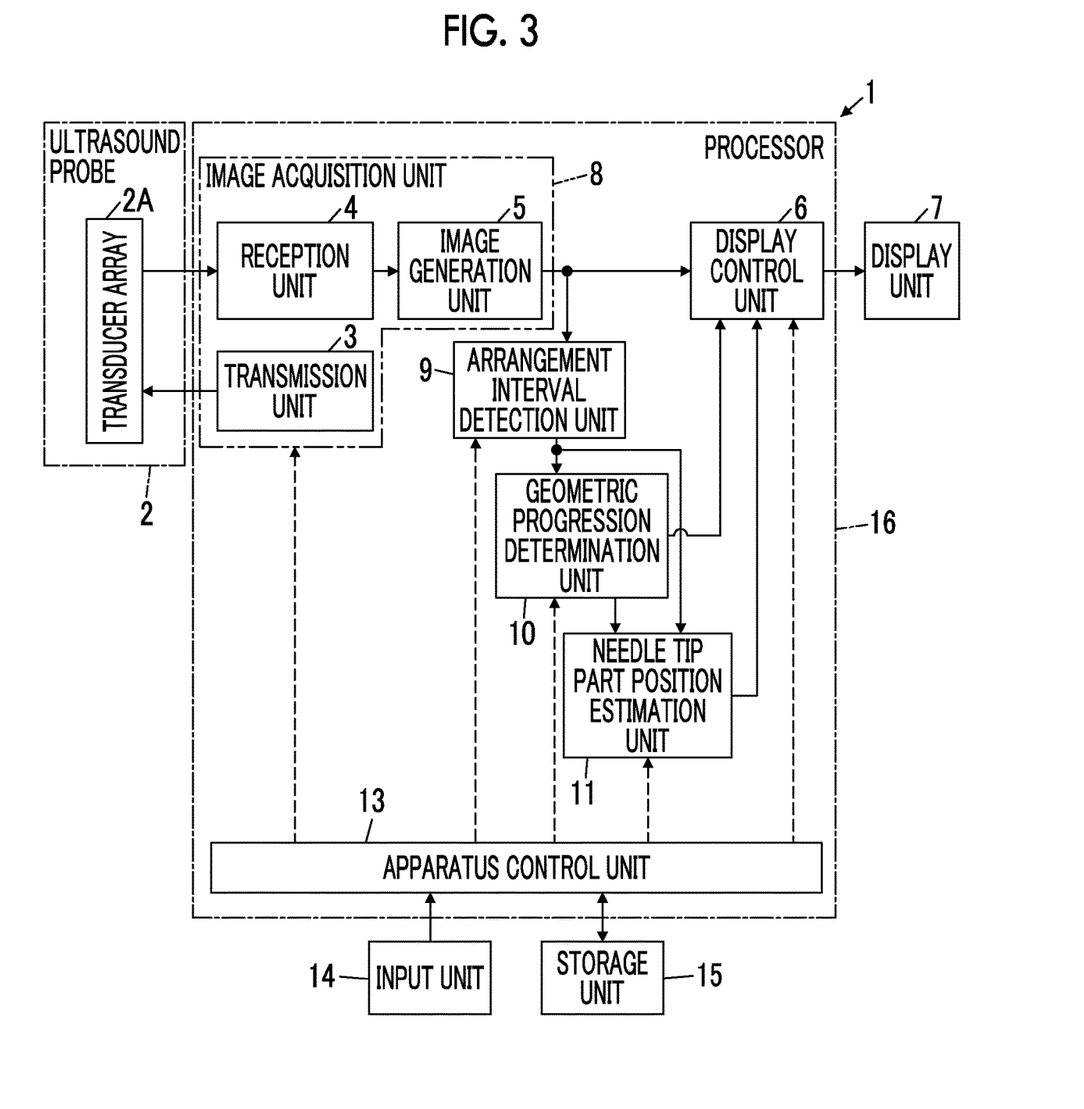
FIG. 3 is a block diagram showing a configuration of an ultrasound diagnostic apparatus according to Embodiment 1 of the present invention.

Next, an ultrasound diagnostic apparatus 1 according to Embodiment 1 of the present invention will be described. The ultrasound diagnostic apparatus 1 images the puncture needle N1 inserted into the subject. As shown in FIG. 3, the ultrasound diagnostic apparatus 1 comprises the ultrasound probe 2 incorporating a transducer array 2A, and a transmission unit 3 and a reception unit 4 are connected to the transducer array 2A. An image generation unit 5, a display control unit 6, and a display unit 7 are sequentially connected to the reception unit 4. Here, an image acquisition unit 8 is constituted of the transmission unit 3, the reception unit 4, and the image generation unit 5. In addition, an arrangement interval detection unit 9 is connected to the image generation unit 5, and a geometric progression determination unit 10 and a needle tip part position estimation unit 11 are connected to the arrangement interval detection unit 9. The display control unit 6 and the needle tip part position estimation unit 11 are connected to the geometric progression determination unit 10. The display control unit 6 is connected to the needle tip part position estimation unit 11.

Further, an apparatus control unit 13 is connected to the display control unit 6, the image acquisition unit 8, the arrangement interval detection unit 9, the geometric progression determination unit 10, and the needle tip part position estimation unit 11, and an input unit 14 and a storage unit 15 are connected to the apparatus control unit 13. Here, the apparatus control unit 13 and the storage unit 15 are connected to each other so that information can be exchanged in both directions.

In addition, a processor 16 is constituted of the display control unit 6, the image acquisition unit 8, the arrangement interval detection unit 9, the geometric progression determination unit 10, the needle tip part position estimation unit 11, and the apparatus control unit 13.

The transducer array 2A of the ultrasound probe 2 shown in FIG. 3 has a plurality of transducers arranged one-dimensionally or two-dimensionally. Each of these transducers transmits an ultrasonic wave in accordance with a drive signal supplied from the transmission unit 3, and receives an ultrasound echo from the subject to output a reception signal. Each transducer is constituted by forming electrodes on both ends of a piezoelectric body made of, for example, a piezoelectric ceramic represented by lead zirconate titanate (PZT), a polymer piezoelectric element represented by poly vinylidene di fluoride (PMN-PT: polyvinylidene fluoride), and a piezoelectric single crystal represented by lead magnesium niobate-lead titanate (PMN-PT: lead magnesium niobate-lead titanate solid solution).

The transmission unit 3 of the image acquisition unit 8 includes, for example, a plurality of pulse generators, and based on a transmission delay pattern selected in accordance with a control signal from the apparatus control unit 13, supplies the drive signals to the plurality of transducers by adjusting the delay amount so that the ultrasonic waves transmitted from the plurality of transducers of the transducer array 2A form an ultrasound beam. In this way, in a case where a pulsed or continuous wave voltage is applied to the electrodes of the plurality of transducers of the transducer array 2A, the piezoelectric body expands and contracts, pulsed or continuous wave ultrasonic waves are generated from the transducers, and an ultrasound beam is formed from a composite wave of the ultrasonic waves.

The transmitted ultrasound beam is reflected at an object such as a part of the subject and propagates toward the transducer array 2A of the ultrasound probe 2. The ultrasound echo propagating toward the transducer array 2A in this way is received by each of the transducers constituting the transducer array 2A. In this case, each transducer constituting the transducer array 2A expands and contracts by receiving the propagating ultrasound echo to generate an electric signal, and outputs these electric signals to the reception unit 4.

Figure 4:
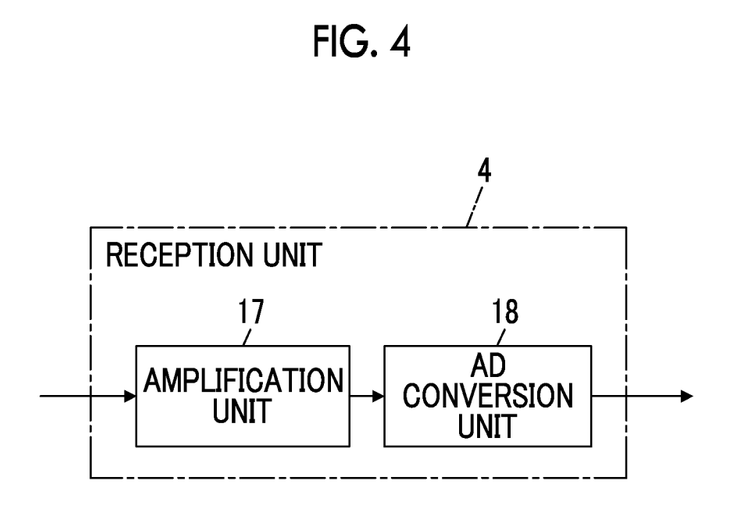
FIG. 4 is a block diagram showing a configuration of a reception unit in Embodiment 1 of the present invention.

The reception unit 4 of the image acquisition unit 8 processes a signal output from the transducer array 2A in accordance with the control signal from the apparatus control unit 13. As shown in FIG. 4, the reception unit 4 has a configuration in which an amplification unit 17 and an analog digital (AD) conversion unit 18 are connected in series. The amplification unit 17 amplifies the signal received from each of the transducers constituting the transducer array 2A, and transmits the amplified signal to the AD conversion unit 18. The AD conversion unit 18 converts the signal transmitted from the amplification unit 17 into a digitized reception signal, and sends these pieces of data to the image generation unit 5 of the image acquisition unit 8.

Figure 5:
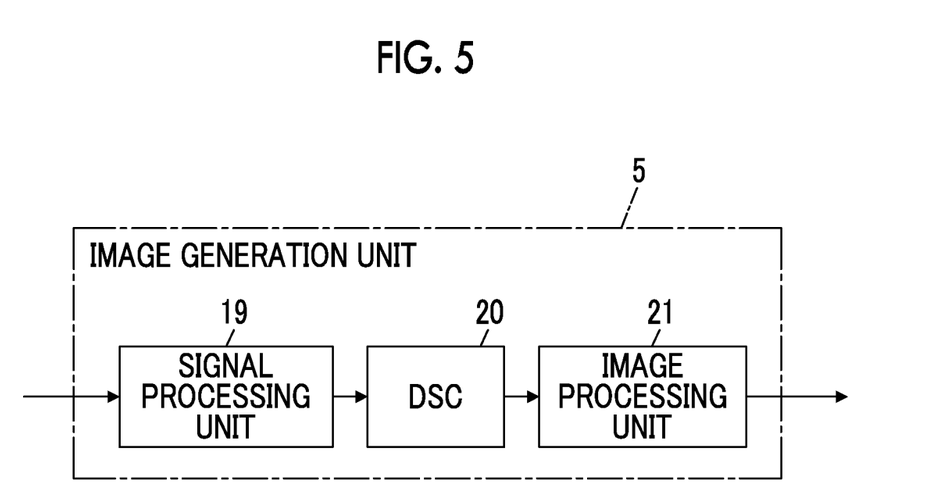
FIG. 5 is a block diagram showing a configuration of an image generation unit in Embodiment 1 of the present invention.

As shown in FIG. 5, the image generation unit 5 of the image acquisition unit 8 has a configuration in which a signal processing unit 19, a digital scan converter (DSC) 20, and an image processing unit 21 are sequentially connected in series. The signal processing unit 19 performs reception focus processing by applying a delay to each piece of data of the reception signal based on a reception delay pattern selected in accordance with the control signal from the apparatus control unit 13, and adding up the results (phase-adjusted addition). By the reception focus processing, a sound ray signal in which a focus of the ultrasound echo is narrowed down to one scanning line is generated. In addition, the signal processing unit 19 corrects attenuation caused by a propagation distance of the generated sound ray signal according to a depth of a position where the ultrasonic wave is reflected, and then performs envelope detection processing to generate a B-mode image signal representing a tissue in the subject. The B-mode image signal generated in this way is output to the DSC 20.

The DSC 20 of the image generation unit 5 generates an ultrasound image by raster-converting the B-mode image signal into an image signal according to a normal television signal scanning method. The image processing unit 21 of the image generation unit 5 performs various kinds of necessary image processing such as brightness correction, gradation correction, sharpness correction, and color correction on the ultrasound image obtained by the DSC 20, and then outputs the ultrasound image to the display control unit 6 and the arrangement interval detection unit 9.

The arrangement interval detection unit 9 of the processor 16 recognizes the plurality of processed parts P1 to P5 of the puncture needle N1 and detects arrangement intervals of the plurality of processed parts P1 to P5 by image analysis of the ultrasound image in which the puncture needle N1 is captured.

The geometric progression determination unit 10 of the processor 16 determines whether or not the arrangement intervals of the plurality of processed parts P1 to P5 detected by the arrangement interval detection unit 9 form the geometric progression with a geometric ratio of 2. The geometric progression determination unit 10 can determine whether or not the arrangement intervals of the plurality of processed parts P1 to P5 form the geometric progression with a geometric ratio of 2, for example, by determining whether or not a plurality of the arrangement intervals detected by the arrangement interval detection unit 9 gradually decrease in one direction along an arrangement direction of the plurality of processed parts P1 to P5 and ratios of the adjacent arrangement intervals is 1:2. Even though a ratio of values of the actually detected arrangement intervals is not exactly 1:2, determination may be made whether or not the geometric progression is formed by approximating the values.

In a case where the geometric progression determination unit 10 determines that the geometric progression with a geometric ratio of 2 is formed, the needle tip part position estimation unit 11 of the processor 16 detects, as the reference point, a point extending from an arrangement position of an optional processed part among the plurality of processed parts P1 to P5 to a tip side of the shaft part S of the puncture needle N1 by an arrangement interval between the optional processed part and a processed part adjacent to a base end side of the shaft part S of the puncture needle N1 with respect to the optional processed part, and estimates a position of the detected reference point as a position of the needle tip part T of the puncture needle N1.

For example, as shown in FIG. 1, since the arrangement interval L1 between the first processed part P1 and the second processed part P2 adjacent to the base end side of the shaft part S of the puncture needle N1 with respect to the first processed part P1 is equal to the distance K1 from the needle tip part T to the first processed part P1, a point extending from the arrangement position of the first processed part P1 to the tip side of the shaft part S of the puncture needle N1 by the arrangement interval L1 is equal to the reference point, that is, the position of the needle tip part T.

Since the plurality of arrangement intervals L1 to L4 form a geometric progression with a geometric ratio of 2, the arrangement interval L2 between the second processed part P2 and the third processed part P3 is equal to twice the arrangement interval L1 adjacent to the needle tip part T side. Further, since the distance K1 from the needle tip part T to the first processed part P1 and the arrangement interval between the first processed part P1 and the second processed part P2 are equal to each other, a distance from the needle tip part T to the processed part P2 is equal to a sum of the distance K1 from the needle tip part T to the first processed part P1 and the arrangement interval L1 between the first processed part P1 and the second processed part P2, that is, twice the arrangement interval L1. Therefore, since the arrangement interval L2 between the second processed part P2 and the third processed part P3 is equal to the distance from the needle tip part T to the second processed part P2, a point extending from the second processed part P2 to the needle tip part T side by the arrangement interval L2 is equal to the reference point, that is, the position of the needle tip part T.

The arrangement interval L3 between the third processed part P3 and the fourth processed part P4 is equal to twice the arrangement interval L2 between the second processed part P2 and the third processed part P3, that is, equal to four times the arrangement interval L1 between the first processed part P1 and the second processed part P2. Further, a distance from the needle tip part T to the third processed part P3 is equal to a sum of the distance K1 from the needle tip part T to the first processed part P1, the arrangement interval L1 between the first processed part P1 and the second processed part P2, and the arrangement interval L2 between the second processed part P2 and the third processed part P3, that is, equal to four times the arrangement interval L1 between the first processed part P1 and the second processed part P2. Therefore, since the arrangement interval L3 between the third processed part P3 and the fourth processed part P4 is equal to the distance from the needle tip part T to the third processed part P3, a point extending from the third processed part P3 to the needle tip part T side by the arrangement interval L3 is equal to the reference point, that is, the position of the needle tip part T.

As described above, the needle tip part position estimation unit 11 can detect, as the reference point, a point extending from an arrangement position of an optional processed part among the plurality of processed parts P1 to P5 to a tip side of the shaft part S of the puncture needle N1 by an arrangement interval between the optional processed part and a processed part adjacent to a base end side of the shaft part S of the puncture needle N1 with respect to the optional processed part, and estimate a position of the detected reference point as a position of the needle tip part T of the puncture needle N1.

In addition, for example, any one of the plurality of processed parts P1 to P5 of the puncture needle N1 may be concealed or disappear in the ultrasound image due to a high-intensity reflection signal, a so-called acoustic shadow, or the like derived from the tissue in the subject. In this case, the geometric progression determination unit 10 determines that the geometric progression with a geometric ratio of 2 is not formed, but in this case, the needle tip part position estimation unit 11 can detect the reference point by estimating the processed part concealed or disappearing due to the high-intensity reflection signal, the acoustic shadow, or the like based on the plurality of arrangement intervals detected by the arrangement interval detection unit 9.

The apparatus control unit 13 of the processor 16 controls each unit of the ultrasound diagnostic apparatus 1 based on a program recorded in advance in the storage unit 15 or the like and an input operation by the user via the input unit 14.

The display control unit 6 of the processor 16, under the control of the apparatus control unit 13, causes the display unit 7 to display the ultrasound image generated by the image generation unit 5 of the image acquisition unit 8, the position of the needle tip part T estimated by the needle tip part position estimation unit 12, and the like.

The display unit 7 of the ultrasound diagnostic apparatus 1 displays the ultrasound image generated by the image acquisition unit 8, the position of the needle tip part T estimated by the needle tip part position estimation unit 12, and the like, and includes, for example, a display device such as a liquid crystal display (LCD) or an organic EL display (organic electroluminescence display). The input unit 14 of the ultrasound diagnostic apparatus 1 is for the user to perform an input operation, and may comprise a keyboard, a mouse, a trackball, a touch pad, a touch panel, and the like.

The storage unit 15 stores an operation program or the like of the ultrasound diagnostic apparatus 1, and may use a recording medium such as a flash memory, a hard disc drive (HDD), a solid state drive (SSD),a flexible disc (FD), a magneto-optical disc (MO disc), a magnetic tape (MT), a random access memory (RAM), a compact disc (CD), a digital versatile disc (DVD), a secure digital card (SD card), and a universal serial bus memory (USB memory), or a server.

The processor 16 having the display control unit 6, the image acquisition unit 8, the arrangement interval detection unit 9, the geometric progression determination unit 10, the needle tip part position estimation unit 11, and the apparatus control unit 13 is constituted of a central processing unit (CPU) and a control program for causing the CPU to perform various kinds of processing, and may be constituted of a field programmable gate array (FPGA), a digital signal processor (DSP), an application specific integrated circuit (ASIC), a graphics processing unit (GPU), or other integrated circuit (IC) or a combination thereof.

The display control unit 6, the image acquisition unit 8, the arrangement interval detection unit 9, the geometric progression determination unit 10, the needle tip part position estimation unit 11, and the apparatus control unit 13 of the processor 16 may be partially or entirely integrated into one CPU or the like.

Figure 6:
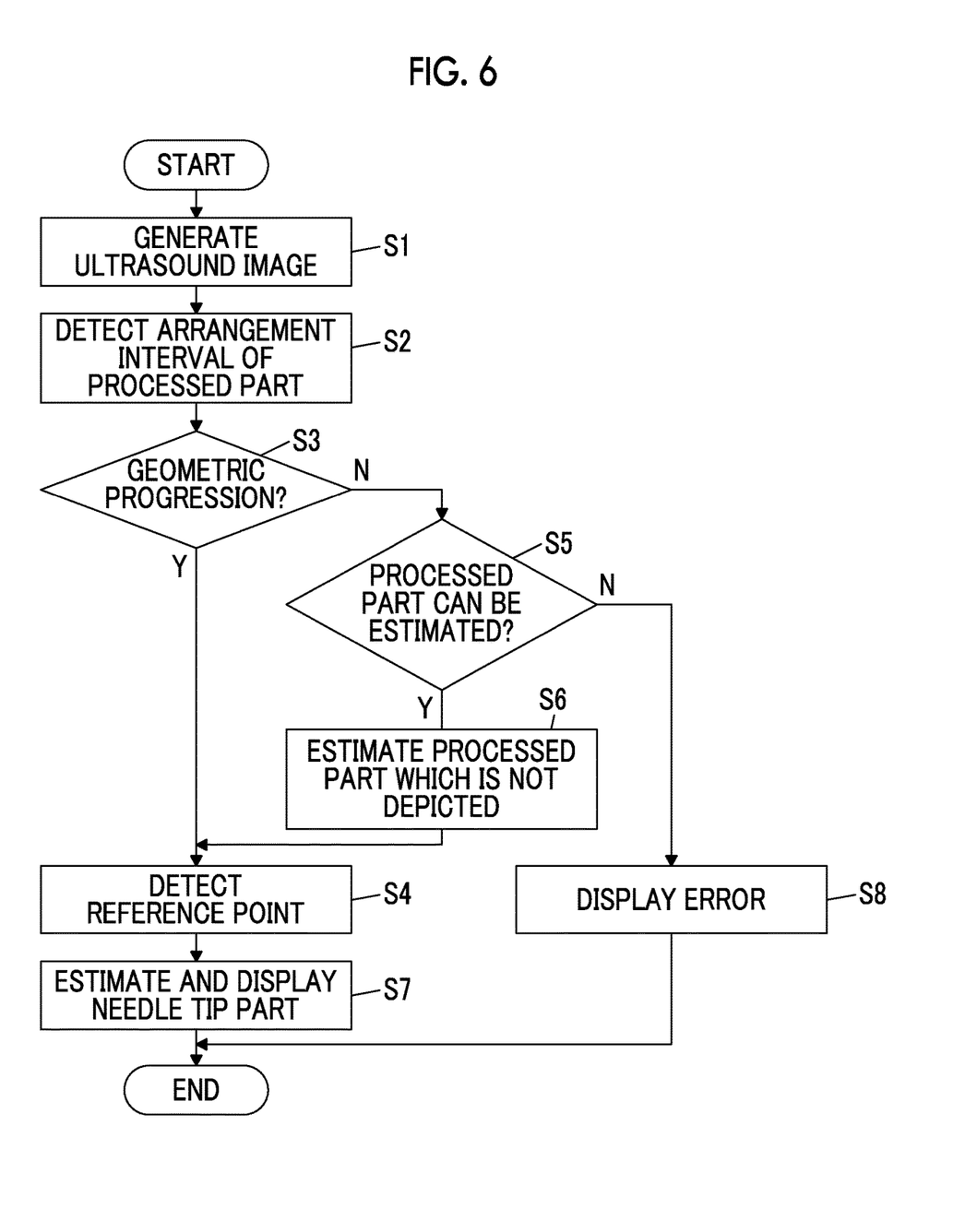
FIG. 6 is a flowchart showing an operation of the ultrasound diagnostic apparatus in Embodiment 1 of the present invention.

Next, the operation of the ultrasound diagnostic apparatus 1 in Embodiment 1 will be described in detail with reference to the flowchart shown in FIG. 6.

First, in step S1, as shown in FIG. 2, an ultrasound beam is applied from the ultrasound probe 2 in contact with the body surface B of the subject toward the puncture needle N1 in the subject, and an ultrasound image is captured. In this case, ultrasound echoes from the subject and the puncture needle N1 are received by the transducer array 2A of the ultrasound probe 2 to generate a reception signal, and the generated reception signal is amplified by the amplification unit 17 of the reception unit 4, and A/D conversion is performed by the A/D conversion unit 18. Further, the reception signal subjected to the A/D conversion is output to the image generation unit 5, and the image generation unit 5 generates an ultrasound image based on the reception signal.

Next, in step S2, the arrangement interval detection unit 9 recognizes the plurality of processed parts P1 to P5 of the puncture needle N1 and detects the arrangement intervals of the plurality of processed parts P1 to P5 by image analysis of the ultrasound image generated in step S1.

In step S3, the geometric progression determination unit 10 determines whether or not the plurality of arrangement intervals detected in step S2 form a geometric progression with a geometric ratio of 2. In a case where determination is made in step S3 that the plurality of arrangement intervals form a geometric progression with a geometric ratio of 2, the process proceeds to step S4.

In step S4, the needle tip part position estimation unit 11 detects, as the reference point, a point extending from an arrangement position of an optional processed part selected among the plurality of processed parts P1 to P5 depicted in the ultrasound image to the tip side of the shaft part S of the puncture needle N1, that is, a point extending in a direction in which lengths of the plurality of arrangement intervals gradually decrease, by an arrangement interval between the selected optional processed part and a processed part adjacent to the base end side of the shaft part S of the puncture needle N1 with respect to the optional processed part, that is, a processed part adjacent in a direction in which the lengths of the plurality of arrangement intervals gradually increase.

For example, in a case where the third processed part P3 is selected among the plurality of processed parts P1 to P5, the needle tip part position estimation unit 11 detects, as the reference point, a point extending from an arrangement position of the third processed part P3 to the tip side of the shaft part S of the puncture needle N1 by the arrangement interval between the third processed part P3 and the fourth processed part P4 adjacent to the base end side of the shaft part S of the puncture needle N1 with respect to the third processed part P3.

In this way, in a case where the process of step S4 is completed, the process proceeds to step S7.

In a case where the geometric progression determination unit 10 determines in step S3 that the geometric progression with a geometric ratio of 2 is not formed, the process proceeds to step S5.

Here, for example, due to a high-intensity reflection signal, a so-called acoustic shadow, or the like derived from the tissue in the subject, a part of the plurality of processed parts P1 to P5 of the puncture needle N1 may not be depicted, such as any one of the plurality of processed parts P1 to P5 being concealed or disappearing in the ultrasound image. In a case where the puncture needle N1 according to Embodiment 1 of the present invention is inserted into the subject, even though a part of the plurality of processed parts P1 to P5 of the puncture needle N1 is not depicted in the ultrasound image, it may be possible to estimate the processed part which is not depicted, and to confirm that the geometric progression with a geometric ratio of 2 is formed by the plurality of processed parts P1 to P5.

Figure 7:
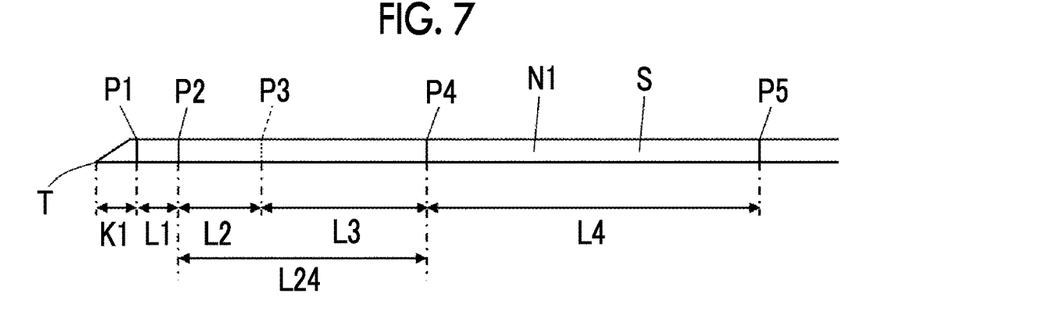
FIG. 7 is a diagram schematically showing a state where one processed part is not depicted in an ultrasound image in Embodiment 1 of the present invention.

For example, as shown in FIG. 7, in a case where the third processed part P3 among the plurality of processed parts P1 to P5 is not depicted in the ultrasound image, the arrangement interval L1 between the first processed part P1 and the second processed part P2, an arrangement interval L24 between the second processed part P2 and the fourth processed part P4, and the arrangement interval L4 between the fourth processed part P4 and the fifth processed part P5 are detected in step S2. In this case, it can be confirmed that the arrangement interval L4 between the fourth processed part P4 and the fifth processed part P5 has a length of eight times the arrangement interval L1 between the first processed part P1 and the second processed part P2. Further, in a case where it is confirmed that the arrangement interval L24 between the second processed part P2 and the fourth processed part P4 is six times the arrangement interval L1 between the first processed part P1 and the second processed part P2, it is estimated that the arrangement interval L24 is a sum of the arrangement interval L2 between the second processed part P2 and the third processed part P3 having a length of twice the arrangement interval L1 and the arrangement interval L3 between the third processed part P3 and the fourth processed part P4 having a length of four times the arrangement interval L1. Thus, for example, even in a case where the third processed part P3 among the plurality of processed parts P1 to P5 is not depicted in the ultrasound image, it can be confirmed that the plurality of processed parts P1 to P5 form the geometric progression with a geometric ratio of 2.

Therefore, in step S5, the geometric progression determination unit 10 determines whether or not the processed part which is not depicted in the ultrasound image can be estimated. In a case where determination is made in step S5 that the processed part which is not depicted in the ultrasound image can be estimated, the process proceeds to step S6.

In step S6, the needle tip part position estimation unit 11 estimates the processed part not depicted in the ultrasound image based on the plurality of arrangement intervals detected in step S2 and positions of the plurality of processed parts depicted in the ultrasound image, and confirms that the plurality of processed parts P1 to P5 form the geometric progression with a geometric ratio of 2. In this way, in a case where the processed part not depicted in the ultrasound image is estimated and it is confirmed that the plurality of processed parts P1 to P5 form the geometric progression with a geometric ratio of 2, the process proceeds to step S4.

In step S4, the needle tip part position estimation unit 11 detects, as the reference point, a point extending from an arrangement position of an optional processed part selected among the arrangement intervals of the plurality of processed part P1 to P5 to the tip side of the shaft part S of the puncture needle N1 by an arrangement interval between the selected optional processed part and a processed part adjacent to the base end side of the shaft part S of the puncture needle N1 with respect to the optional processed part while taking into consideration the position of the processed part estimated in step S6.

In this way, in a case where the process of step S4 is completed, the process proceeds to step S7.

In step S7, the needle tip part position estimation unit 11 estimates the reference point detected in step S4 as the position of the needle tip part T of the puncture needle N1.

Here, since the plurality of arrangement intervals L1 to L4 form a geometric progression with a geometric ratio of 2, for example, the arrangement interval L3 between the third processed part P3 and the fourth processed part P4 is equal to four times the arrangement interval L1 between the first processed part P1 and the second processed part P2. In addition, since the distance K1 from the needle tip part T to the first processed part P1 is equal to the arrangement interval L1 between the first processed part P1 and the second processed part P2, and the arrangement interval L2 between the second processed part P2 and the third processed part P3 is equal to twice the arrangement interval L1 between the first processed part P1 and the second processed part P2, for example, the distance from the needle tip part T to the third processed part P3, that is, the sum of the distance K1 from the needle tip part T to the first processed part P1, the arrangement interval L1 between the first processed part P1 and the second processed part P2, and the arrangement interval L2 between the second processed part P2 and the third processed part P3 is equal to four times the arrangement interval L1 between the first processed part P1 and the second processed part P2.

Therefore, since the arrangement interval L3 between the third processed part P3 and the fourth processed part P4 is equal to the distance from the needle tip part T to the third processed part P3, the needle tip part position estimation unit 11 can estimate, as the position of the needle tip part T, a point extending from an arrangement position of the third processed part P3 to the tip side of the shaft part S of the puncture needle N1, that is, the reference point by, for example, an arrangement interval between the third processed part P3 and the fourth processed part P4 adjacent to the base end side of the shaft part S of the puncture needle N1 with respect to the third processed part P3.

Figure 8:
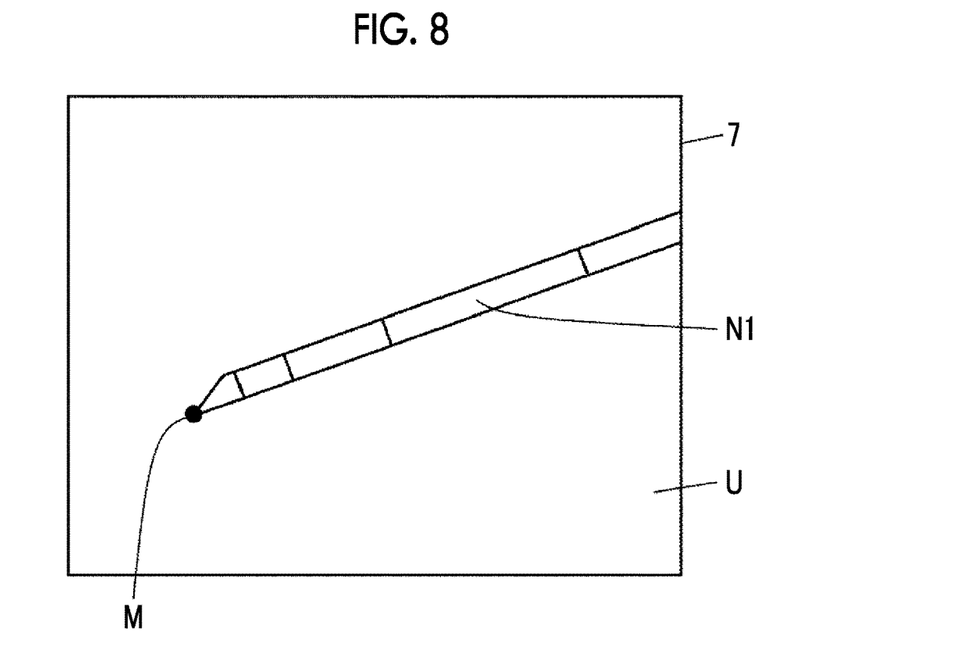
FIG. 8 is a diagram schematically showing a state where a position of a needle tip part is displayed on the ultrasound image in Embodiment 1 of the present invention.

In addition, the needle tip part position estimation unit 11 superimposes the estimated position of the needle tip part T on the ultrasound image generated in step Si and causes the display unit 7 to display the image. For example, as shown in FIG. 8, the needle tip part position estimation unit 12 superimposes a tip mark M representing the position of the needle tip part T of the puncture needle N1 on an ultrasound image U and displays the image on the display unit 7. In the example shown in FIG. 8, the tip mark M is indicated by a black circle for description.

In a case where the process of step S7 is completed in this way, the operation of the ultrasound diagnostic apparatus 1 ends.

In addition, in step S5, in a case where the geometric progression determination unit 10 determines that the plurality of arrangement intervals detected in step S2 are not allowed to form a geometric progression with a geometric ratio of 2 and that a processed part which is not depicted in the ultrasound image U cannot be estimated, the process proceeds to step S8. Here, for example, in a case where two or more arrangement intervals which are integral multiples of each other among the plurality of processed parts P1 to P5 are not detected in step S2 and it cannot be confirmed that the plurality of processed parts P1 to P5 form a geometric progression with a geometric ratio of 2, or in a case where a puncture needle having no processed parts arranged in accordance with a geometric progression with a geometric ratio of 2 is inserted into the subject, instead of the puncture needle N1 according to Embodiment 1 of the present invention, the plurality of arrangement intervals detected in step S2 are not allowed to form a geometric progression with a geometric ratio of 2.

In step S8, the geometric progression determination unit 10 displays, although not shown, occurrence of an error on the display unit 7. In this way, in a case where the process of step S8 is completed, the operation of the ultrasound diagnostic apparatus 1 ends.

As described above, the puncture needle N1 according to Embodiment 1 of the present invention comprises the plurality of processed parts P1 to P5 forming a geometric progression with a geometric ratio of 2 in which values gradually decrease toward the needle tip part T, the distance K1 between the needle tip part T and the first processed part P1 is equal to the arrangement interval L1 between the first processed part P1 and the second processed part P2 which is second closest to the needle tip part T. Therefore, for example, the ultrasound diagnostic apparatus 1 easily estimates the position of the needle tip part T and displays the estimated position of the needle tip part T on the display unit 7. Thus, the user can accurately grasp the position of the needle tip part T of the puncture needle N1 by confirming the display unit 7.

According to the ultrasound diagnostic apparatus 1 according to Embodiment 1 of the present invention, the plurality of processed parts P1 to P5 are recognized to detect the arrangement intervals of the plurality of processed parts P1 to P5 by image analysis of the ultrasound image U, whether or not the detected arrangement intervals of the plurality of processed parts form a geometric progression with a geometric ratio of 2 is determined, and in a case where determination is made that the detected plurality of arrangement intervals form the geometric progression with a geometric ratio of 2, a point extending from an arrangement position of an optional processed part selected among the plurality of processed parts P1 to P5 depicted in the ultrasound image to the tip side of the shaft part S of the puncture needle N1 by an arrangement interval between the selected optional processed part and a processed part adjacent to the base end side of the shaft part S of the puncture needle N1 with respect to the optional processed part is detected as the reference point, and the detected reference point is estimated as the position of the needle tip part T. Therefore, the position of the needle tip part T can be estimated with high accuracy.

Further, according to the ultrasound diagnostic apparatus 1 according to Embodiment 1 of the present invention, even in a case where any one of the plurality of processed parts P1 to P5 of the puncture needle N1 is concealed or disappears in the ultrasound image U due to a high-intensity reflection signal, an acoustic shadow, or the like derived from the tissue in the subject, the needle tip part position estimation unit 11 estimates a position of the concealed or disappearing processed part and confirms that the plurality of arrangement intervals L1 to L4 form a geometric progression with a geometric ratio of 2. Therefore, the position of the needle tip part T can be estimated with high accuracy as in the case where the plurality of processed parts P1 to P5 are depicted in the ultrasound image U.

In the example shown in FIG. 1, although five processed parts P1 to P5 are formed in the shaft part S from the needle tip part T of the puncture needle N1 toward a base end part of the shaft part S, the number of processed parts is not limited to five. The number of processed parts formed in the shaft part S may be more than five, and for example, a plurality of processed parts (not shown) forming a geometric progression with a geometric ratio of 2 together with the first processed part P1 to the fifth processed part P5 may be provided on the base end part side from the processed part P5. In addition, the number of processed parts may be less than five, and may be, for example, four.

Further, the needle tip part position estimation unit 11 selects an optional processed part from the plurality of processed parts P1 to P5, detects, as the reference point, a point extending from the selected processed part to the tip side of the shaft part S of the puncture needle N1 by an arrangement interval between the selected processed part and a processed part adjacent to the base end side of the shaft part S of the puncture needle N1 from the selected processed part, and estimates the detected reference point as the position of the needle tip part T. The closer the selected processed part is located to the tip side of the shaft part S, the less likely it is to be affected by mechanical deflection of the shaft part S, and thus, detection accuracy of the reference point, that is, estimation accuracy of the needle tip part T is improved. Therefore, it is desirable that the needle tip part position estimation unit 11 selects, for example, a processed part located closest to the tip side of the shaft part S among the plurality of processed parts depicted in the ultrasound image U and the plurality of estimated processed parts, and detects the reference point.

The needle tip part position estimation unit 11 can acquire a plurality of detection results of the reference point by, for example, selecting the plurality of processed parts depicted in the ultrasound image U and the plurality of estimated processed parts, respectively, and detect an average value of the acquired plurality of detection results as the position of the reference point.

In this case, the needle tip part position estimation unit 11 can change a color of the tip mark M shown in FIG. 8, for example, in accordance with a value representing variation of the plurality of detection results, for example, an average value of the distances between the detected reference points. For example, the needle tip part position estimation unit 11 can display the tip mark M in red in a case where the value representing the variation of the plurality of detection results is larger than a predetermined value, and can display the tip mark M in blue in a case where the value representing the variation of the plurality of detection results is equal to or smaller than a predetermined value. Thus, the user can easily grasp the estimation accuracy of the needle tip part T.

For example, in a case where the plurality of processed parts depicted in the ultrasound image U and the plurality of estimated processed parts are selected and the obtained plurality of detection results of the reference point are averaged, the needle tip part position estimation unit 11 can calculate an average value by weighting the position of the detected reference point as the processed part is located closer to the tip side of the shaft part S of the puncture needle N1. Thus, the estimation accuracy of the needle tip part T can be improved.

Embodiment 2

In the puncture needle N1 of Embodiment 1, although the reference point is equal to the needle tip part T, the position of the reference point can be set closer to the base end side of the shaft part S than the needle tip part T.

Figure 9:
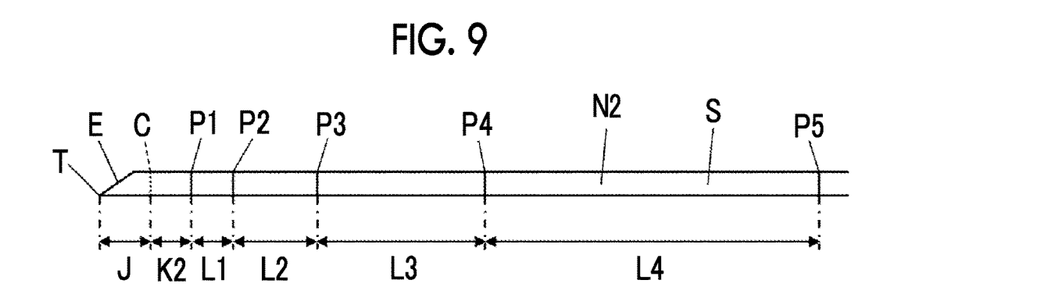
FIG. 9 is a diagram showing a puncture needle according to Embodiment 2 of the present invention.

As shown in FIG. 9, although a puncture needle N2 according to Embodiment 2 of the present invention, similarly to the puncture needle N1 of Embodiment 1 shown in FIG. 1, comprises a shaft part S and a needle tip part T disposed at a tip of the shaft part S, and a plurality of processed parts P1 to P5 are arranged and formed on the shaft part S, a position of a reference point C is set closer to the base end side of the shaft part S than the needle tip part T. The reference point C is set at a position separated from the needle tip part T by a predetermined distance J, and a distance K2 from the reference point C to the first processed part P1 is equal to the arrangement interval L1 between the first processed part P1 and the second processed part P2. In addition, an arrangement interval L1 between the first processed part P1 and the second processed part P2, an arrangement interval L2 between the second processed part P2 and the third processed part P3, an arrangement interval L3 between the third processed part P3 and the fourth processed part P4, and an arrangement interval L4 between the fourth processed part P4 and the fifth processed part P5 form a geometric progression with a geometric ratio of 2.

Therefore, in a case where it is confirmed that the plurality of arrangement intervals L1 to L4 form a geometric progression with a geometric ratio of 2 and any position of the plurality of processed parts P1 to P5 is known, the position of the reference point C can be estimated. Further, by acquiring the distance J from the needle tip part T to the reference point C, the position of the needle tip part T can be estimated based on the acquired distance J and the estimated position of the reference point C.

Figure 10:
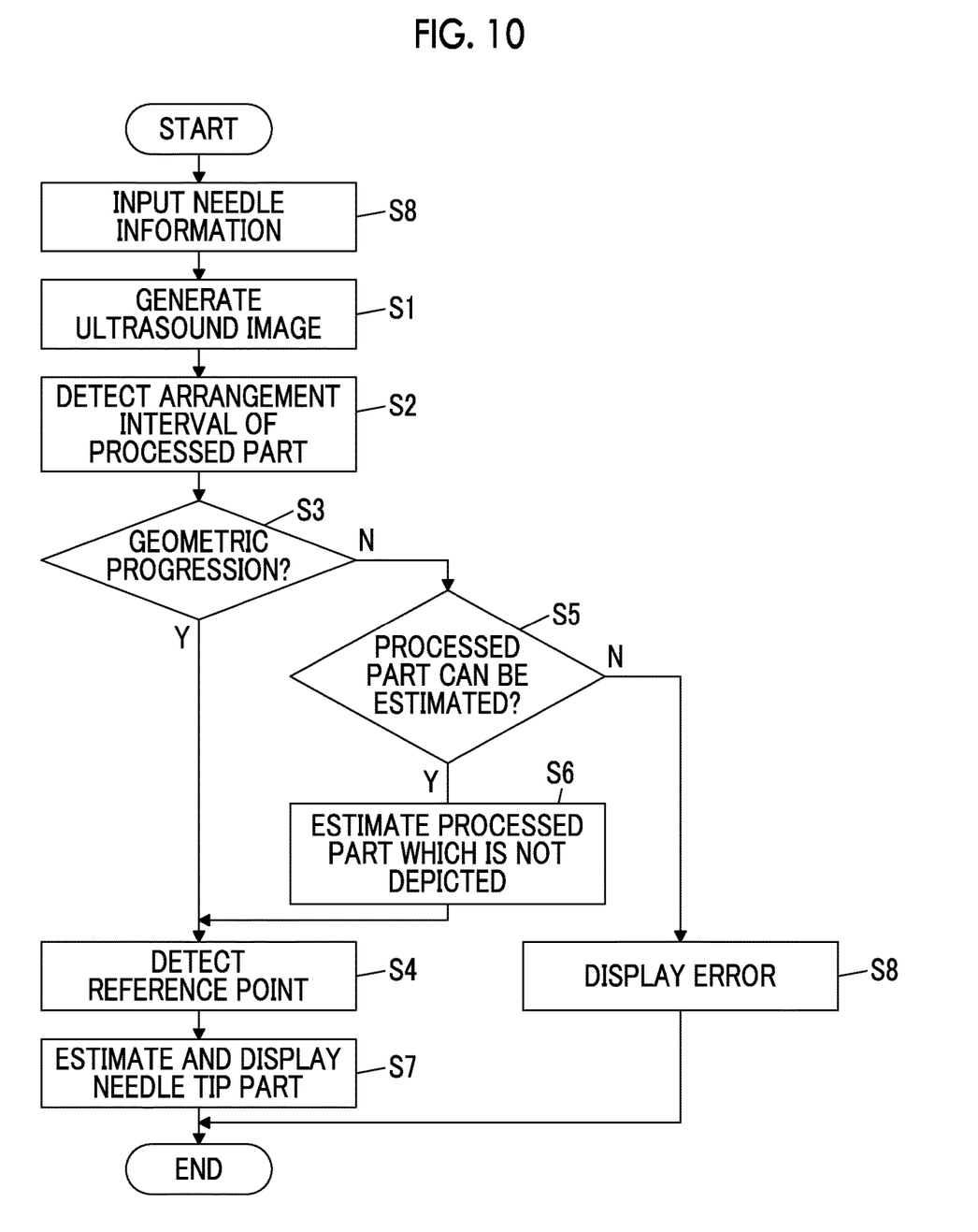
FIG. 10 is a flowchart showing an operation of an ultrasound diagnostic apparatus according to Embodiment 2 of the present invention.

Next, the operation of the ultrasound diagnostic apparatus 1 of estimating the position of the needle tip part T of the puncture needle N2 will be described with reference to the flowchart shown in FIG. 10.

First, in step S8, needle information, which is information of the puncture needle N2, is input by the user via the input unit 14. The needle information input here includes the predetermined distance J from the needle tip part T to the reference point C.

Next, in step S1, as in the aspect shown in FIG. 2, an ultrasound beam is applied from the ultrasound probe 2 in contact with the body surface B of the subject toward the puncture needle N2 in the subject, and an ultrasound image U is captured.

In step S2, the arrangement interval detection unit 9 recognizes the plurality of processed parts P1 to P5 of the puncture needle N2 and detects the arrangement intervals of the plurality of processed parts P1 to P5 by image analysis of the ultrasound image U generated in step S1.

In step S3, the geometric progression determination unit 10 determines whether or not the plurality of arrangement intervals detected in step S2 form a geometric progression with a geometric ratio of 2. In a case where determination is made in step S3 that the plurality of arrangement intervals form a geometric progression with a geometric ratio of 2, the process proceeds to step S4.

In step S4, the needle tip part position estimation unit 11 detects, as the reference point C, a point extending from an arrangement position of an optional processed part selected among the arrangement intervals of the plurality of processed part P1 to P5 depicted in the ultrasound image to the tip side of the shaft part S of the puncture needle N1 by an arrangement interval between the selected optional processed part and a processed part adjacent to the base end side of the shaft part S of the puncture needle N1 with respect to the optional processed part.

In a case where the reference point C is detected in this way, the process proceeds to step S7.

In a case where determination is made in step S3 that the geometric progression with a geometric ratio of 2 is not formed by the plurality of arrangement intervals detected in step S2, the process proceeds to step S5.

In step S5, the geometric progression determination unit 10 determines whether or not the processed part which is not depicted in the ultrasound image U can be estimated. In a case where determination is made in step S5 that the processed part which is not depicted on the ultrasound image U can be estimated, the process proceeds to step S6.

In step S6, the needle tip part position estimation unit 11 estimates the processed part not depicted in the ultrasound image based on the plurality of arrangement intervals detected in step S2 and positions of the plurality of processed parts depicted in the ultrasound image, and confirms that the plurality of processed parts P1 to P5 form the geometric progression with a geometric ratio of 2. In this way, in a case where the processed part not depicted in the ultrasound image is estimated and it is confirmed that the plurality of processed parts P1 to P5 form the geometric progression with a geometric ratio of 2, the process proceeds to step S4.

In step S4, the needle tip part position estimation unit 11 detects, as the reference point C, a point extending from an arrangement position of an optional processed part selected among the arrangement intervals of the plurality of processed part P1 to P5 to the tip side of the shaft part S of the puncture needle N1 by an arrangement interval between the selected optional processed part and a processed part adjacent to the base end side of the shaft part S of the puncture needle N1 with respect to the optional processed part while taking into consideration the position of the processed part estimated in step S6.

In this way, in a case where the process of step S4 is completed, the process proceeds to step S7.

In step S7, the needle tip part position estimation unit 11 estimates, as the position of the needle tip part T, a point extending from the position of the reference point C detected in step S4 to the tip side of the shaft part S of the puncture needle N2 by the predetermined distance J, based on the needle information input in step S8. Further, as in the aspect shown in FIG. 8, the needle tip part position estimation unit 11 superimposes a tip mark M representing the estimated position of the needle tip part T on the ultrasound image U generated in step S1 and displays the image on the display unit 7.

In a case where the process of step S7 is completed in this way, the operation of the ultrasound diagnostic apparatus 1 ends.

In addition, in step S5, in a case where the geometric progression determination unit 10 determines that the plurality of arrangement intervals detected in step S2 are not allowed to form a geometric progression with a geometric ratio of 2 and that a processed part which is not depicted in the ultrasound image U cannot be estimated, the process proceeds to step S8.

In step S8, the geometric progression determination unit 10 displays, although not shown, occurrence of an error on the display unit 7. In this way, in a case where the process of step S8 is completed, the operation of the ultrasound diagnostic apparatus 1 ends.

As described above, the puncture needle N2 according to Embodiment 2 of the present invention comprises the plurality of processed parts P1 to P5 forming a geometric progression with a geometric ratio of 2 in which values gradually decrease toward the needle tip part T, the reference point C is set at a position located on the needle tip part T side from the first processed part P1 closest to the needle tip part T among the plurality of processed parts P1 to P5 and separated from the needle tip part T by the predetermined distance, the distance K2 between the reference point C and the first processed part P1 is equal to the arrangement interval L1 between the first processed part P1 and the second processed part P2 which is second closest to the needle tip part T. Therefore, for example, the ultrasound diagnostic apparatus 1 easily detects the reference point C, easily estimates the position of the needle tip part T, and displays the estimated position of the needle tip part T on the display unit 7. Thus, the user can accurately grasp the position of the needle tip part T of the puncture needle N1 by confirming the display unit 7.

In the puncture needle N2 of Embodiment 2, although the reference point C is formed at a position separated from the needle tip part T by the predetermined distance J, a length of the predetermined distance J is not particularly limited.

However, the shorter the predetermined distance J, the closer the first processed part P1 is formed to the needle tip part T, and the less likely it is to be affected by deflection of the puncture needle N2 or the like in a case where the position of the needle tip part T is estimated. Therefore, estimation accuracy of the needle tip part T can be improved. Therefore, from the viewpoint of improving the estimation accuracy of the needle tip part T, the length of the predetermined distance J is preferably shorter, for example, the distance K2 from the position of the reference point C to the first processed part P1 or less.

Although not shown, the ultrasound diagnostic apparatus 1 comprises a needle information acquisition unit that acquires needle information of the puncture needle N2 by scanning the puncture needle N2, reading a bar code attached to a packaging bag of the puncture needle N2, or the like. Thus, for example, the user can save time and effort of manually inputting the needle information via the input unit 14.

Embodiment 3

The ultrasound diagnostic apparatus 1 according to Embodiment 1 has a configuration in which the ultrasound probe 2 and the display unit 7 are directly connected to the processor 16, but for example, the ultrasound probe 2, the display unit 7, and the processor 16 can be indirectly connected to one another via a network.

Figure 11:
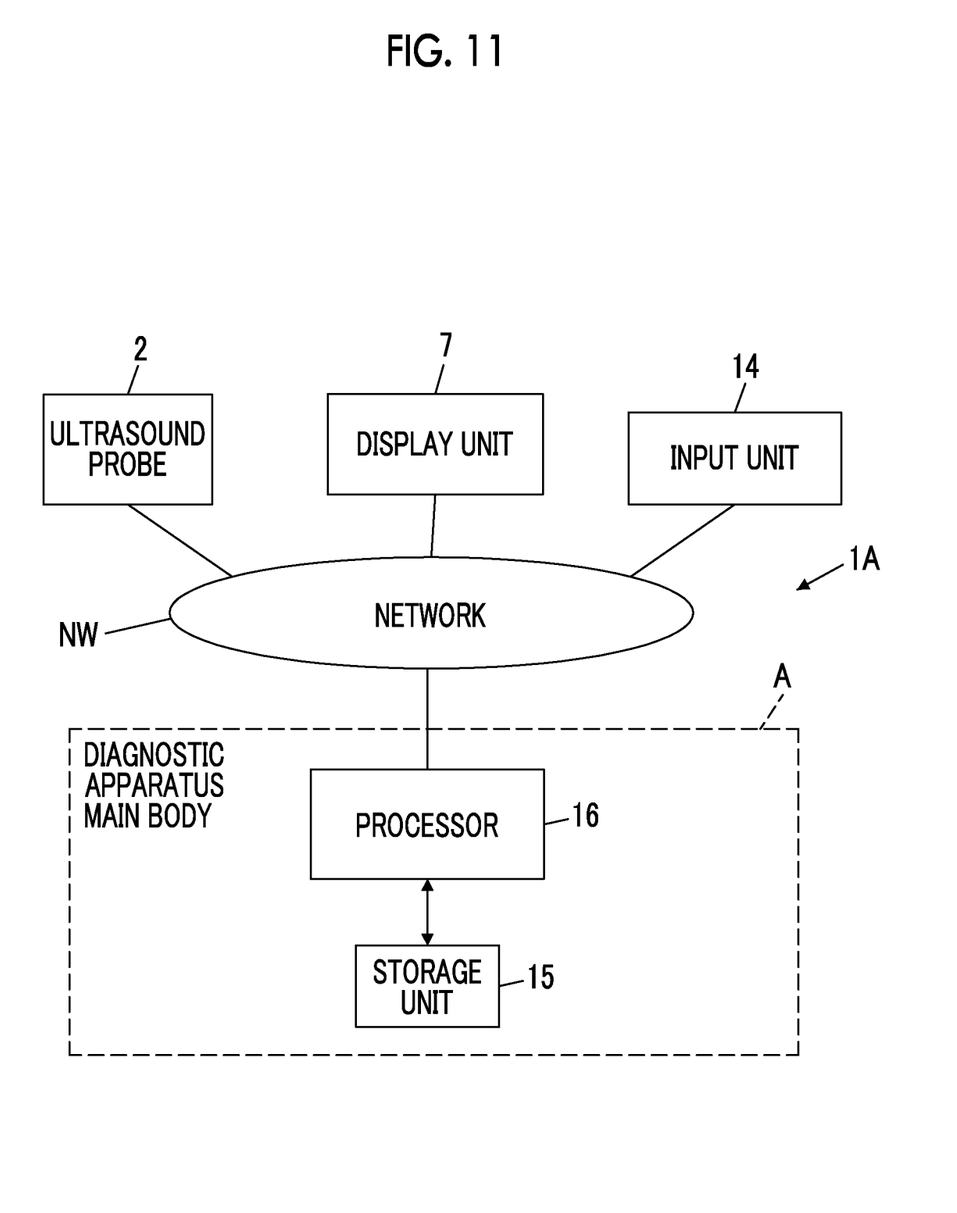
FIG. 11 is a block diagram showing a configuration of an ultrasound diagnostic apparatus according to Embodiment 3 of the present invention.

As shown in FIG. 11, in an ultrasound diagnostic apparatus 1A according to Embodiment 3, the ultrasound probe 2, the display unit 7, and the input unit 14 are connected to a diagnostic apparatus main body A via a network NW. The diagnostic apparatus main body A is the ultrasound diagnostic apparatus 1 shown in FIG. 3, excluding the ultrasound probe 2, the display unit 7, and the input unit 14.

Here, in a case where an ultrasound beam is transmitted from the ultrasound probe 2 toward the inside of the subject in a state where the ultrasound probe 2 is pressed against the body surface B of the subject by the user, an ultrasound echo reflected in the inside of the subject is received by the transducer array 2A of the ultrasound probe 2 to generate a reception signal. The ultrasound probe 2 transmits the generated reception signal to the diagnostic apparatus main body A via the network NW. The reception signal transmitted from the ultrasound probe 2 in this way is received by the image acquisition unit 8 of the processor 16 of the diagnostic apparatus main body A via the network NW, and the image acquisition unit 8 generates the ultrasound image U based on the reception signal.

The ultrasound image U generated by the image acquisition unit 8 is sent to the display control unit 6 and the arrangement interval detection unit 9. The display control unit 6 performs predetermined processing on the ultrasound image U received from the image acquisition unit 8, and further, transmits the ultrasound image U subjected to the predetermined processing to the display unit 7 via the network NW. In this way, the ultrasound image U transmitted from the display control unit 6 of the processor 16 of the diagnostic apparatus main body A is received by the display unit 7 via the network NW and displayed on the display unit 7.

The arrangement interval detection unit 9 recognizes the plurality of processed parts P1 to P5 of the puncture needle N1 and detects the arrangement intervals of the recognized plurality of processed parts P1 to P5 by image analysis of the ultrasound image U received from the image acquisition unit 8.

The geometric progression determination unit 10 determines whether or not the arrangement intervals detected by the arrangement interval detection unit 9 form the geometric progression with a geometric ratio of 2.

The needle tip part position estimation unit 11 detects, as the reference point, a point extending from an arrangement position of an optional processed part among the plurality of processed parts P1 to P5 to a tip side of the shaft part S of the puncture needle N1 by an arrangement interval between the optional processed part and a processed part adjacent to a base end side of the shaft part S of the puncture needle N1 with respect to the optional processed part, and estimates a position of the detected reference point as a position of the needle tip part T of the puncture needle N1.

As described above, according to the ultrasound diagnostic apparatus 1A according to Embodiment 3 of the present invention, even in a case where the ultrasound probe 2, the display unit 7, the input unit 14, and the diagnostic apparatus main body A are connected via the network NW, similarly to the ultrasound diagnostic apparatus 1 of Embodiment 1, the plurality of processed parts P1 to P5 are recognized to detect the arrangement intervals of the plurality of processed parts P1 to P5 by image analysis of the ultrasound image U, whether or not the detected arrangement intervals of the plurality of processed parts form a geometric progression with a geometric ratio of 2 is determined, and in a case where determination is made that the detected plurality of arrangement intervals form the geometric progression with a geometric ratio of 2, a point extending from an arrangement position of an optional processed part selected among the plurality of processed parts P1 to P5 depicted in the ultrasound image to the tip side of the shaft part S of the puncture needle N1 by an arrangement interval between the selected optional processed part and a processed part adjacent to the base end side of the shaft part S of the puncture needle N1 with respect to the optional processed part is detected as the reference point, and the detected reference point is estimated as the position of the needle tip part T. Therefore, the position of the needle tip part T can be estimated with high accuracy.

Since the ultrasound probe 2, the display unit 7, and the input unit 14 are connected to the diagnostic apparatus main body A via the network NW, the diagnostic apparatus main body A can be used as a so-called remote server. Thus, for example, the user can perform ultrasound diagnosis of the subject by preparing only the ultrasound probe 2, the display unit 7, and the input unit 14 at the user's hand, and thus convenience in the ultrasound diagnosis can be improved.

In addition, for example, in a case where a portable thin computer called a so-called tablet is used as the display unit 7 and the input unit 14, the user can more easily perform the ultrasound diagnosis of the subject, and convenience in the ultrasound diagnosis can be further improved.

Although the ultrasound probe 2, the display unit 7, and the input unit 14 are connected to the diagnostic apparatus main body A via the network NW, the ultrasound probe 2, the display unit 7, the input unit 14, and the diagnostic apparatus main body A may be wire-connected or wirelessly connected to the network NW.

Although it has been described that the aspect of Embodiment 3 is applied to Embodiment 1, the same can be applied to Embodiment 2.

EXPLANATION OF REFERENCES 1, 1A: ultrasound diagnostic apparatus
2: ultrasound probe 2A: transducer array
3: transmission unit
4: reception unit
5: image generation unit
6: display control unit
7: display unit
8: image acquisition unit
9: arrangement interval detection unit
10: geometric progression determination unit
11: needle tip part position estimation unit
13: apparatus control unit
14: input unit
15: storage unit
16: processor
17: amplification unit
18: AD conversion unit
19: signal processing unit
20: DSC
21: image processing unit
A: diagnostic apparatus main body
B: body surface
J, K1, K2: distance
L1, L2, L24, L3, L4: arrangement interval
M: tip mark
N1, N2: puncture needle
NW: network
P1: first processed part
P2: second processed part
P3: third processed part
P4: fourth processed part
P5: fifth processed part
S: shaft part
T: needle tip part
U: ultrasound image

What is claimed is:

1. An ultrasound diagnostic apparatus comprising:
a display device that displays an ultrasound image in which a puncture needle is captured,
where the puncture needle comprises a shaft part, a needle part disposed at a tip of the shaft part, and a plurality of grooves that are arranged on an outer peripheral part of the shaft part along a length direction of the shaft part and form a geometric progression with a geometric ratio of 2 in which arrangement intervals decrease toward the needle tip part,
the plurality of grooves include a first groove that is closest to the needle tip part and a second groove that is second closest to the needle tip part, and
a distance between a reference point which is located on a position away from the first groove toward the needle tip part and is located at a predetermined distance from the needle tip part, and the first groove is equal to a distance between the first groove and the second groove; and
a processor configured to
recognize the plurality of grooves of the puncture needle and detect arrangement intervals of the plurality of grooves based on the ultrasound image;
determine the detected arrangement intervals of the plurality of grooves form a geometric progression with a geometric ratio of 2;
detect, as a reference point, a first point extending from an arrangement position of an optional groove among the plurality of grooves toward the needle tip part of the puncture needle by one of the arrangement intervals between the optional groove and one of the plurality of grooves adjacent to an opposite side to the needle tip part with respect to the optional groove; and
estimate a position of the needle tip part based on a position of the detected reference point.

2. The ultrasound diagnostic apparatus according to claim 1,
wherein the display device displays the ultrasound image in which the puncture needle that the predetermined distance is 0 mm and the reference point is the needle tip part is captured, and
the processor is further configured to estimate the position of the reference point as the position of the needle tip part.

3. The ultrasound diagnostic apparatus according to claim 1,
wherein the processor is further configured to estimate a second point extending from the position of the reference point toward the needle tip part by the predetermined distance as the position of the needle tip part.

4. The ultrasound diagnostic apparatus according to claim 1,
wherein the processor is further configured to display the estimated position of the needle tip part on the display device.

5. The ultrasound diagnostic apparatus according to claim 1, further comprising:
an ultrasound probe;
wherein the processor is further configured to acquire the ultrasound image by performing transmission and reception of an ultrasound beam between the ultrasound probe and a subject,
wherein the display device displays the acquired ultrasound image, and
the processor is further configured to recognize the plurality of grooves of the puncture needle and detect the arrangement intervals of the plurality of grooves based on-the ultrasound image.

6. An ultrasound diagnostic apparatus comprising:
a display device that displays an ultrasound image in which a puncture needle is captured,
where the puncture needle comprises a shaft part, a needle part disposed at a tip of the shaft part, and a plurality of grooves that are arranged on an outer peripheral part of the shaft part along a length direction of the shaft part and form a geometric progression with a geometric ratio of 2 in which arrangement intervals decrease toward the needle tip part,
the plurality of grooves include a first groove that is closest to the needle tip part and a second groove that is second closest to the needle tip part, and
a distance between the needle tip part and the first groove is equal to a distance between the first groove and the second groove; and
a processor configured to
recognize the plurality of grooves of the puncture needle and detect arrangement intervals of the plurality of grooves based on the ultrasound image;
determine the detected arrangement intervals of the plurality of grooves form a geometric progression with a geometric ratio of 2;
detect, as the needle tip part, a first point extending from an arrangement position of an optional groove among the plurality of grooves toward the needle tip part by one of the arrangement intervals between the optional groove and one of the plurality of grooves adjacent to an opposite side to the needle tip part with respect to the groove, in a case where determination is made that the geometric progression is formed.

7. An ultrasound diagnostic apparatus comprising:
a display device that displays an ultrasound image in which a puncture needle is captured,
where the puncture needle comprises a shaft part, a needle part disposed at a tip of the shaft part, and a plurality of grooves that are arranged on an outer peripheral part of the shaft part along a length direction of the shaft part and form a geometric progression with a geometric ratio of 2 in which arrangement intervals decrease toward the needle tip part,
the plurality of grooves are formed all around the outer peripheral part of the shaft part,
the plurality of grooves include a first groove that is closest to the needle tip part and a second groove that is second closest to the needle tip part, and
a distance between a reference point which is located on a position away from the first groove toward the needle tip part and is located at a predetermined distance from the needle tip part, and the first groove is equal to a distance between the first groove and the second groove; and
a processor configured to
recognize the plurality of grooves of the puncture needle and detect arrangement intervals of the plurality of grooves based on the ultrasound image;
determine the detected arrangement intervals of the plurality of grooves form a geometric progression with a geometric ratio of 2;
detect, as a reference point, a first point extending from an arrangement position of an optional groove among the plurality of grooves toward the needle tip part of the puncture needle by one of the arrangement intervals between the optional groove and one of the plurality of grooves adjacent to an opposite side to the needle tip part with respect to the optional groove and estimate a position of the needle tip part based on a position of the detected reference point, in a case where determination is made that the geometric progression is formed.

8. The ultrasound diagnostic apparatus according to claim 7,
wherein the display device displays the ultrasound image in which the puncture needle that the predetermined distance is 0 mm and the reference point is the needle tip part is captured, and
the processor is further configured to estimate the position of the reference point as the position of the needle tip part.

9. The ultrasound diagnostic apparatus according to claim 7,
wherein the processor is further configured to estimate a second point extending from the position of the reference point toward the needle tip part by the predetermined distance as the position of the needle tip part.

10. An ultrasound diagnostic apparatus comprising:
a display device that displays an ultrasound image in which a puncture needle is captured,
where the puncture needle comprises a shaft part, a needle part disposed at a tip of the shaft part, and a plurality of grooves that are arranged on an outer peripheral part of the shaft part along a length direction of the shaft part and form a geometric progression with a geometric ratio of 2 in which arrangement intervals decrease toward the needle tip part,
the plurality of grooves are formed all around the outer peripheral part of the shaft part,
the plurality of grooves include a first groove that is closest to the needle tip part and a second groove that is second closest to the needle tip part, and a distance between the needle tip part and the first groove is equal to a distance between the first groove and the second groove; and
a processor configured to
recognize the plurality of grooves of the puncture needle and detect arrangement intervals of the plurality of grooves based on the ultrasound image;
determine the detected arrangement intervals of the plurality of grooves form a geometric progression with a geometric ratio of 2;
detect, the needle tip part, a first point extending from an arrangement position of an optional groove among the plurality of grooves toward the needle tip part by one of the arrangement intervals between the optional groove and one of the plurality of grooves adjacent to an opposite side to the needle tip part with respect to the optional groove, in a case where determination is made that the geometric progression is formed.

11. A control method of an ultrasound diagnostic apparatus comprising:
displaying an ultrasound image in which a puncture needle is captured,
where the puncture needle comprises a shaft part, a needle part disposed at a tip of the shaft part, and a plurality of grooves that are arranged on an outer peripheral part of the shaft part along a length direction of the shaft part and form a geometric progression with a geometric ratio of 2 in which arrangement intervals decrease toward the needle tip part,
the plurality of grooves include a first groove that is closest to the needle tip part and a second groove that is second closest to the needle tip part, and
a distance between a reference point which is located on a position away from the first groove toward the needle tip part and is located at a predetermined distance from the needle tip part, and the first groove is equal to a distance between the first groove and the second groove;
recognizing the plurality of grooves of the puncture needle and detecting arrangement intervals of the plurality of grooves based on the ultrasound image;
determining the detected arrangement intervals of the plurality of grooves form the geometric progression with a geometric ratio of 2;
detecting, as the reference point, a point extending from an arrangement position of an optional groove among the plurality of grooves toward the needle tip part by an arrangement interval between the optional groove and one of the plurality of grooves adjacent to an opposite side to the needle tip part with respect to the optional groove; and
estimating a position of the needle tip part based on a position of the detected reference point.

\* \* \* \* \*